United States Patent
Segovia Martinez et al.

(10) Patent No.: US 9,445,203 B2
(45) Date of Patent: Sep. 13, 2016

(54) SIGNAL PROCESSOR FOR A HEARING DEVICE AND METHOD FOR OPERATING A HEARING DEVICE

(71) Applicant: OTICON MEDICAL A/S, Smørum (DK)

(72) Inventors: Manuel Segovia Martinez, Vallauris (FR); Jonathan Laudanski, Vallauris (FR); Dan Gnansia, Vallauris (FR); Yves Wenzinger, Vallauris (FR); Bertrand Philppon, Vallauris (FR); Emilie Daanouni, Vallauris (FR)

(73) Assignee: OTICON MEDICAL A/S, Smorum (DK)

( * ) Notice: Subject to any disclaimer, the term of this patent is extended or adjusted under 35 U.S.C. 154(b) by 0 days.

(21) Appl. No.: 14/328,228

(22) Filed: Jul. 10, 2014

(65) Prior Publication Data

US 2015/0016647 A1    Jan. 15, 2015

(30) Foreign Application Priority Data

Jul. 11, 2013   (EP) .................................... 13176154

(51) Int. Cl.
| | |
|---|---|
| *H04R 1/00* | (2006.01) |
| *H04R 25/00* | (2006.01) |
| *A61N 1/36* | (2006.01) |
| *H04R 3/00* | (2006.01) |

(52) U.S. Cl.
CPC ........... *H04R 25/50* (2013.01); *A61N 1/36032* (2013.01); *H04R 3/002* (2013.01)

(58) Field of Classification Search
CPC . H04R 25/606; H04R 2225/025; A61N 1/08

USPC .................................. 381/312–313, 317–318
See application file for complete search history.

(56) References Cited

U.S. PATENT DOCUMENTS

| | | | |
|---|---|---|---|
| 4,207,441 A | 6/1980 | Ricard et al. | |
| 6,453,200 B1 | 9/2002 | Koslar | |
| 2003/0012392 A1* | 1/2003 | Armstrong | ........... H04R 25/356 381/321 |
| 2005/0069162 A1 | 3/2005 | Haykin et al. | |
| 2006/0122664 A1 | 6/2006 | Sacha et al. | |
| 2009/0067651 A1 | 3/2009 | Klinkby et al. | |

(Continued)

FOREIGN PATENT DOCUMENTS

EP          2 217 004 A1    8/2010

*Primary Examiner* — Jesse Elbin
*Assistant Examiner* — Julie X Dang
(74) *Attorney, Agent, or Firm* — Birch, Stewart, Kolasch & Birch, LLP (57) ABSTRACT

A signal processor for a hearing device with an implantable stimulator having two or more electrodes for emitting electric charge pulses to neural-fibers of an individual. The processor has a signal path comprising an input circuit adapted to receive an acoustic-signal from the surroundings and provide at least one corresponding input audio-signal; a filter bank adapted to provide at least one band-limited audio-signal in dependence on the at least one input audio-signal; and a noise filter adapted to attenuate undesired signal components in the at least one band-limited audio-signal and to provide at least one corresponding noise-filtered signal. The processor is characterised in that the portion of the signal path preceding the noise filter neither causes an effective level compression nor an effective level expansion of the at least one noise-filtered signal when the at least one noise-filtered signal is derived from an acoustic signal having a level within the comfortable acoustic range.

19 Claims, 4 Drawing Sheets

(56) References Cited

U.S. PATENT DOCUMENTS

| | | | |
|---|---|---|---|
| 2009/0076569 A1* | 3/2009 | Busby | A61N 1/36032 607/57 |
| 2009/0112051 A1* | 4/2009 | Miller, III | A61B 5/721 600/25 |
| 2010/0246886 A1 | 9/2010 | Swain et al. | |
| 2011/0064241 A1* | 3/2011 | Kulkarni | A61N 1/36032 381/94.2 |
| 2012/0109006 A1* | 5/2012 | James | A61N 1/36032 600/559 |
| 2012/0308060 A1 | 12/2012 | Pontoppidan | |
| 2013/0090074 A1* | 4/2013 | Christensen | H03J 1/008 455/120 |

\* cited by examiner

SIGNAL PROCESSOR FOR A HEARING DEVICE AND METHOD FOR OPERATING A HEARING DEVICE

TECHNICAL FIELD

The present invention relates to a signal processor for a hearing device and to a method for operating a hearing device. More specifically, the present invention relates to a signal processor for a hearing device for electric stimulation of nerve cells and to a method for operating such a hearing device.

The invention may e.g. be useful in applications such as a hearing aid for compensating a hearing-impaired person's loss of hearing capability or a listening device for augmenting a normal-hearing person's hearing capability.

BACKGROUND ART

U.S. Pat. No. 4,207,441 discloses an auditory prosthesis equipment comprising n electrode sets implanted in the cochlea at n discrete locations chosen to allow the brain to identify n discrete frequencies in the sound range. Signals collected by a microphone are passed through a compressor to adapt the dynamic range of the sound information (e.g. 60 dB) to the dynamic characteristics of the ear (e.g. 4 dB). An analysing network transforms the compressed signal into n analysis signals using filters with frequencies corresponding to the frequencies identifiable by the brain. An amplitude calculating network calculates the mean value of the amplitudes of each analysis signal, and a signal forming network generates n pulse signals in dependence on the analysis signals. A logic circuit provides a raster signal with width-modulated pulses in dependence on the n mean values, the n pulse signals and a matching network for preadjustment to individual users. The raster signal is transmitted inductively to an implanted receiver, which sequentially transmits electric pulses to respective electrode sets in the n electrode sets such that the energy transmitted in each electric pulse corresponds to the energy indicated in the respective pulse in the raster signal.

The compression of the microphone signals in the disclosed auditory prosthesis equipment inherently changes the frequency composition in the signals, and thus creates artefacts in the n analysis signals provided by the subsequent frequency filtering. Furthermore, the signal processing in the disclosed auditory prosthesis equipment does not provide any specific enhancement of speech signals compared to other acoustic signals.

SUMMARY OF THE INVENTION

The present invention provides a signal processor that allows implementing a hearing device that does not suffer from the above problems. The invention also provides a method for operating a hearing device, which overcomes the above problems.

The invention is achieved by the invention defined in the accompanying independent claims and as explained in the following description. The invention is further achieved by the embodiments defined in the dependent claims and in the detailed description of the invention.

In the present context, a "hearing device" refers to a device, such as e.g. a hearing aid or a listening device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears in the form of electric signals transferred directly or indirectly to the cochlear nerve, to other sensory nerves and/or to the auditory cortex of the user.

A hearing device may comprise a single unit or several units communicating electronically with each other. Each of the one or more units of a hearing device may be configured to be worn in any known way, e.g. behind the ear, entirely or partly arranged in the pinna and/or in the ear canal, as an entirely or partly implanted unit, etc.

More generally, a hearing device comprises an input transducer for receiving an acoustic signal from a user's surroundings and providing a corresponding input audio signal, a signal processing circuit for processing the input audio signal and an output means for providing an audible signal to the user in dependence on the processed audio signal. Some hearing devices may comprise multiple input transducers, e.g. for providing direction-dependent audio signal processing. In some hearing devices, the output means may comprise one or more output electrodes for providing electric signals. In some hearing devices, the output electrodes may be implanted in the cochlea or on the inside of the skull bone and may be adapted to provide the electric signals to the hair cells of the cochlea, to one or more hearing nerves and/or to the auditory cortex.

A "hearing system" refers to a system comprising one or two hearing devices, and a "binaural hearing system" refers to a system comprising one or two hearing devices and being adapted to cooperatively provide audible signals to both of the user's ears. In a hearing system or a binaural hearing system, one or both of the hearing devices may comprise other output means in addition to output electrodes in order to provide audible signals e.g. in the form of acoustic signals radiated into the user's outer ears or acoustic signals transferred as mechanical vibrations to the user's inner ears through the bone structure of the user's head and/or through parts of the middle ear. In such hearing devices, the output means may comprise an output transducer, such as e.g. a loudspeaker for providing an air-borne acoustic signal or a vibrator for providing a structure-borne or liquid-borne acoustic signal. In a binaural hearing system, the output electrodes may be omitted in one hearing device comprising such other output means.

Hearing systems or binaural hearing systems may further comprise "auxiliary devices", which communicate with the hearing devices and affect and/or benefit from the function of the hearing devices. Auxiliary devices may be e.g. remote controls, remote microphones, audio gateway devices, mobile phones, public-address systems, car audio systems or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person.

As used herein, the singular forms "a", "an", and "the" are intended to include the plural forms as well (i.e. to have the meaning "at least one"), unless expressly stated otherwise. It will be further understood that the terms "has", "includes", "comprises", "having", "including" and/or "comprising", when used in this specification, specify the presence of stated features, integers, steps, operations, elements and/or components, but do not preclude the presence or addition of one or more other features, integers, steps, operations, elements, components and/or groups thereof. It will be understood that when an element is referred to as being "connected" or "coupled" to another element, it can be directly connected or coupled to the other element, or intervening elements may be present, unless expressly stated otherwise. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF THE DRAWINGS

The invention will be explained in more detail below in connection with preferred embodiments and with reference to the drawings in which.

The figures are schematic and simplified for clarity, and they just show details, which are essential to the understanding of the invention, while other details are left out. Throughout, like reference numerals and/or names are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from this detailed description.

DETAILED DESCRIPTION OF THE INVENTION

Figure 1:
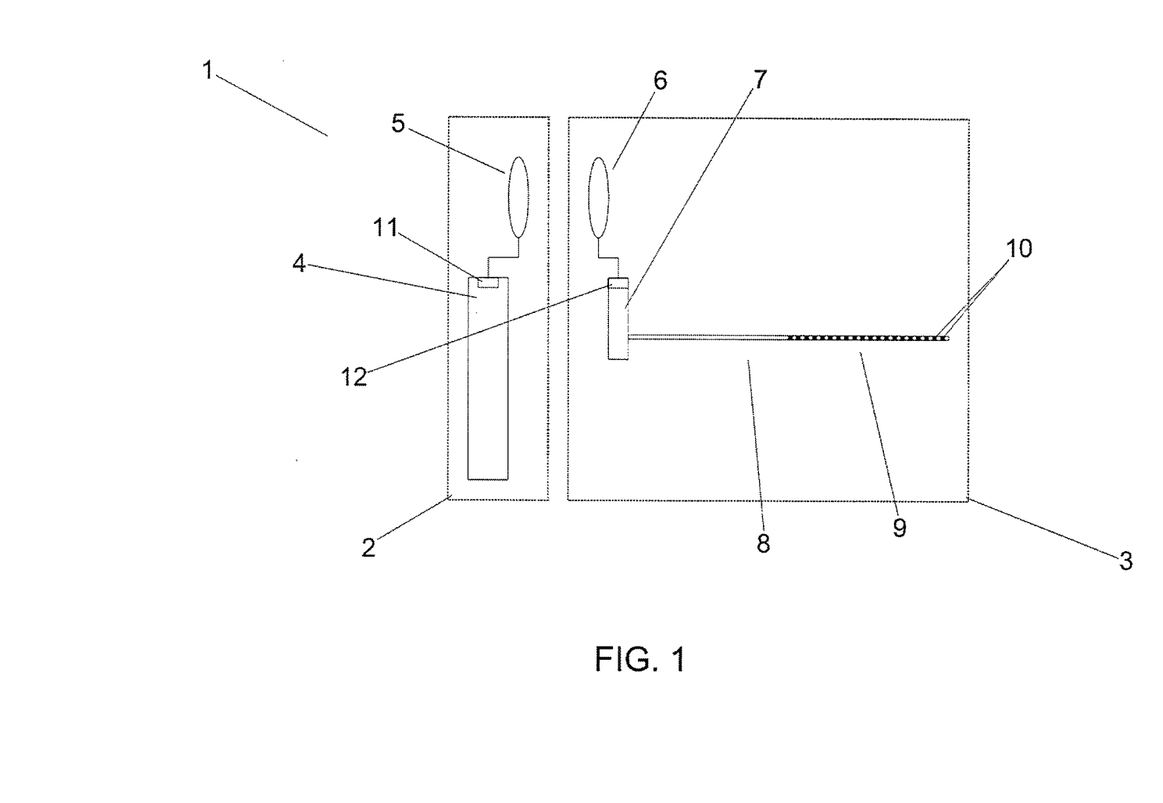
FIG. 1 shows an a hearing device according to an embodiment of the invention.

The embodiment of a hearing device 1 shown in FIG. 1 comprises a wearable device 2 and an implantable stimulator 3. The wearable device 2 comprises a pre-processor 4, a transmission coil 5 and a battery (not shown) for powering the electronic circuits of the wearable device 2 and/or the electronic circuits of the implantable stimulator 3. The implantable stimulator 3 comprises a reception coil 6, a post-processor 7 and a flexible electrode carrier 8. The flexible electrode carrier 8 comprises an electrode array 9 with twenty electrodes 10. In other embodiments, the number of electrodes 10 may be different. The pre-processor 4 comprises a transmitter 11, and the post-processor 7 comprises a corresponding receiver 12.

The wearable device 2 is adapted to be worn on the body of the user of the hearing device 1, such that the pre-processor 4 may receive an acoustic signal from the user's surroundings and pre-process the acoustic signal. The transmitter 11 encodes the pre-processed signal and transmits the encoded signal to the implantable stimulator 3 by means of the transmission coil 5. The implantable stimulator 3 is adapted to be implanted in the body of the user, e.g. on the inside of the skull or in the cochlea, with the electrodes 10 adjacent to neural fibres such that electric charge pulses emitted by the electrodes 10 may stimulate these neural fibres and thus create a sensation in the user, preferably in the form of a perceived sound. The reception coil 6 is adapted to be arranged such that the post-processor 7 may receive the encoded signal from the transmitter 11 by means of the reception coil 6 and the receiver 12, decode the encoded signal by means of the receiver 12 and provide electric charge pulses to the neural fibres through the electrodes 10 of the flexible electrode carrier 8 in dependence on the decoded signal. The hearing device 1 may thus create sensations in the user in dependence on the acoustic signal.

The hearing device 1 controls the stimulation, and thereby the sensation in the user, by varying the pulse emission times and/or the amount of electric charge emitted in the electric charge pulses. The latter may preferably be done by varying the duration and/or the amplitude of the electric charge pulses. Such variations of the charge amount is typically perceived as variations in the strength of the signal, e.g. as loudness in the case that the stimulated neural fibres belong to the auditory nerve. The hearing device 1 is preferably further adapted to stimulate at least two different sets of neural fibres in order to create a further dimension in the perception of the sensation. For example, stimulating different sets of neural fibres in the auditory nerve may create perception of different sound frequencies in the user. In the following, the term "auditory channel" denotes any distinct set of neural fibres of a particular user that may be stimulated by the hearing device 1.

Figure 2:
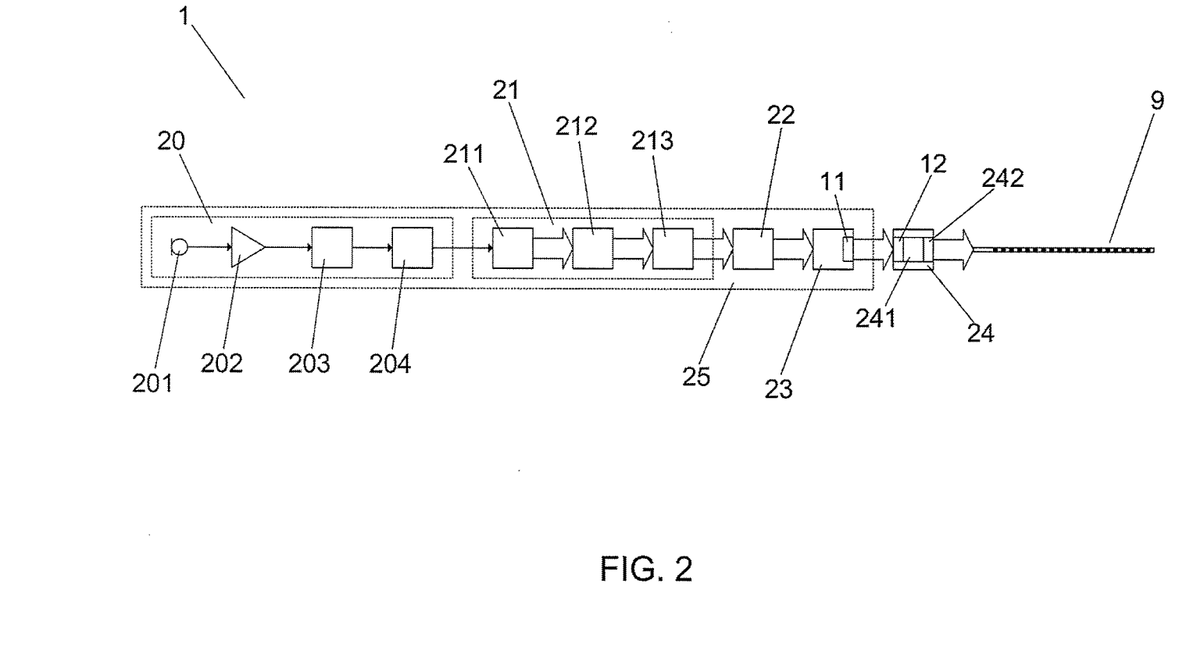
FIG. 2 shows a functional block diagram of the hearing device shown in FIG. 1 according to an embodiment of the invention.

As shown in the functional block diagram in FIG. 2, the hearing device 1 comprises an input circuit 20, a filter bank 21, a noise filter 22, a pulse controller 23, a pulse generator 24 and the electrode array 9. The input circuit 20 comprises an input transducer 201, a preamplifier 202, a digitiser 203 and a pre-emphasis filter 204. The filter bank 21 comprises an FFT converter 211, an energy estimator 212 and a channel combiner 213. The input circuit 20, the filter bank 21, the noise filter 22 and the pulse controller 23 together constitute a signal processor 25. In the shown embodiment, the signal processor 25 is comprised by the pre-processor 4. In other embodiments, the signal processor 25 may be comprised partly by the pre-processor 4 and partly by the post-processor 7, and in such embodiments the signal processor 25 may further comprise the pulse generator 24.

The input transducer 201 is arranged such that it may receive an acoustic signal from the user's surroundings and provide a corresponding electric input signal. The preamplifier 202 amplifies the electric input signal, and the digitiser 203 digitises the amplified input signal. The pre-emphasis filter 204 pre-filters the digitised input signal, such that low and high audio frequencies are emphasised in order to achieve a frequency characteristic more like the human ear's natural frequency characteristic. The pre-emphasis filter 204 is preferably programmable in order to allow e.g. an audiologist to adapt the frequency characteristic to the preferences and the hearing capability of the user. The input circuit 20 provides the pre-filtered input signal as an input audio signal to the filter bank 21. In other embodiments, the input circuit 20 may provide the electric input signal, the amplified input signal or the digitised input signal as the input audio signal. In other embodiments, the input circuit 20 may comprise further input transducers 201, preamplifiers 202, digitisers 203, pre-emphasis filters 204, wireless receivers, etc., that allow the hearing device 1 to receive and process acoustic signals from further sources and/or to achieve directional preference for specific spatial directions.

The FFT converter 211 transforms the input audio signal from a time-domain representation to a frequency-domain representation by means of a Fast Fourier Transformation (FFT), thus providing a number, e.g. 32, 64 or 128, of frequency-bin signals. The energy estimator 212 squares the respective frequency-bin signals and provides a corresponding number of frequency-energy signals indicating the instantaneous energy in the respective frequency-bin signals. The channel combiner 213 combines the frequency-energy signals, or any subset hereof, into a number of frequency channels, each comprising one band-limited audio signal. The number of frequency channels preferably equals the maximum number of auditory channels that may be stimulated by the electrodes 10 in the electrode array 9 and is thus typically lower than the number of frequency-bin signals and frequency-energy signals. In other embodiments, the number of frequency channels may be larger, or alternatively, lower than the maximum number of stimulatable auditory channels. The number of frequency channels may e.g. equal 1, 2, 4, 8, 16, 20, 24, 28 or 32. In other embodiments, other well known time-to-frequency domain converters may replace the FFT converter 211, such as e.g. a bank of narrow-band filters.

The channel combiner 213 preferably performs the combining for each frequency channel by adding one or more of the frequency-energy signals into the respective band-limited audio signal. Within any frequency channel, the channel combiner 213 may weigh the respective frequency-energy signals differently, e.g. to accommodate for user preferences. The channel combiner 213 preferably combines the frequency-energy signals such that the band-limited audio signals comprise different subsets of frequency-energy signals. In other embodiments, one or more subsets of the total set of band-limited audio signals may comprise identical subsets of frequency-energy signals. The channel combiner 213 preferably combines the frequency-energy signals such that any frequency-energy signal is at most combined into one of the band-limited audio signals. In other embodiments, the same frequency-energy signal may be combined into two or more of the band-limited audio signals.

The filter bank 21 thus provides at least one band-limited audio signal in dependence on the input audio signal. The filter bank 21 preferably provides two or more band-limited audio signals such that the user may distinguish between acoustic signals having different frequency content. The filter bank 21 is preferably programmable in order to allow e.g. an audiologist to allocate specific frequency-bin signals to specific band-limited audio signals and thus to specific auditory channels depending on the preferences and the hearing capability of the user.

The noise filter 22 attenuates undesired signal components in the band-limited audio signals and provides corresponding noise-filtered signals. Preferably, one noise-filtered signal is provided for each frequency channel and thus for each band-limited audio signal. The FFT transformation of the input audio signal in the filter bank 21 is performed using a limited time window in order to keep the time delay through the hearing device at a reasonably low level. This inherently causes pure tones to smear out on adjacent frequency bands, and since the frequency-domain signals are not converted back into time-domain signals, which would otherwise remove or reduce the smearing, the smearing is preferably removed or at least reduced by the noise filter 22. Several methods for such "side-lobe cleaning" are already known in the art, and any of these may be implemented in the noise filter 22.

Furthermore, the noise filter 22 preferably removes 50 Hz or 60 Hz noise signals that may be induced in the transmission coil 5 and/or the reception coil 6 when the coils 5, 6 are close to mains power wiring and thus, depending on the actual configuration of the hearing device 1 (see further below), may also appear in the band-limited audio signals. Furthermore, the noise filter 22 preferably removes noise signals with a level below a noise-floor threshold in order to prevent that the user perceives the noise floor of the surroundings when no sounds of interest are present. The noise filter 22 is preferably programmable in order to allow e.g. an audiologist to adapt the noise attenuation to the preferences and the hearing capability of the user.

Preferably, the pulse controller 23 causes the pulse generator 24 to provide one stream of electric charge pulses for each noise-filtered signal. The pulse controller 23 computes emission times for the electric charge pulses, preferably such that the emission times coincide with a regular time interval of e.g. 1 ms or 2 ms. In other embodiments, alternative time schemes may be used as is well known in the art. The pulse controller 23 further computes target charge amounts E (see FIG. 3) for the individual electric charge pulses in dependence on the noise-filtered signals. The computation of the target charge amounts E is explained in detail in the description of FIG. 3 further below.

The pulse generator 24 generates electric charge pulses and provides the electric charge pulses to the electrodes 10, such that the emitted electric charge in each pulse corresponds to the respective target charge amount E. The pulse generator 24 preferably provides each electric charge pulse as a current flowing out through one or more electrodes 10, those electrodes 10 thus having positive polarity, and back through one or more other electrodes 10, those electrodes 10 thus having negative polarity, thereby causing the current to flow from the positive electrodes 10 to the negative electrodes 10 through the tissue and thereby stimulating neural fibres in or adjacent to the tissue.

The pulse generator 24 preferably comprises a pulse generator circuit 241 and a switching circuit 242 operable to electrically connect the pulse generator circuit 241 to the electrodes 10 of the electrode array 9 in different stimulation configurations in order to cause the pulse current to flow through different tissue portions and thereby stimulate different sets of neural fibres. The pulse generator 24 may thus stimulate different auditory channels and create different sensations in the user by changing the stimulation configuration of the pulse generator 24 and/or the electrode array 9. Instead of, or in addition to, switching the electrodes 10, multiple, individually controllable pulse generator circuits 241 may be used to achieve the same or further configurability.

In one or more stimulation configurations, a first electrode 10 may have positive polarity and a second, adjacent electrode 10 may have negative polarity while the remaining electrodes 10 are disconnected from the pulse generator circuit 241 and thus have neutral polarity, such that the pulse current flows from the first to the second electrode 10. In one or more other stimulation configurations, a first electrode 10 may have positive or negative polarity while all of the remaining electrodes 10 have respectively negative or positive polarity, such that the pulse current flows respectively from the first electrode 10 to all of the remaining electrodes 10 or in the opposite direction. In one or more further stimulation configurations, a first electrode 10 and all electrodes 10 between the first electrode 10 and the respective end of the electrode array 9 may have positive polarity while a second, adjacent electrode 10 and all electrodes 10 between the second electrode 10 and the respective other end of the electrode array 9 may have negative polarity, such that the pulse current flows substantially between two portions of the electrode array 9, which together comprise all of the electrodes 10. Further stimulation configurations, such as mixtures of the above stimulation configurations, may be used if desired.

Preferably, each frequency channel or pulse stream is allocated to a predefined auditory channel, and the predefined auditory channels and their allocation are preferably chosen such that sensations perceived by the user are similar to the sensations a normal-hearing person would perceive when subjected to acoustic signals within the frequency ranges of the corresponding band-limited audio signals.

The pulse generator 24 preferably provides the electric charge pulses such that they each start at a respective computed emission time. The charge amount provided by each pulse may be controlled by varying the duration and/or the amplitude of the electric charge pulses. The pulse generator 24 preferably provides the electric charge pulses as bi-phase pulses, i.e. as pairs of pulses with the two pulses of each pair following immediately after each other and having opposite polarity and thus opposite current direction, in order to prevent a build-up over time of electric potential in the tissue. In this case, the two pulses of each bi-phase pulse preferably each provides one half of the respective target charge amount E.

The pre-processor 4 preferably comprises the signal processor 25, and thus the input circuit 20, the filter bank 21, the noise filter 22 and the pulse controller 23, as well as a transmitter 11. The pulse controller 23 provides a pulse signal indicating the computed emission times and the computed target charge amounts E for the individual electric charge pulses. The transmitter 11 receives the pulse signal as the pre-processed signal, encodes the pulse signal and transmits the encoded pulse signal to the implantable stimulator 3 through the transmission coil 5. The transmission is preferably performed using near-field magnetic induction (NFMI) signals that are known to penetrate skin and tissue without significant attenuation. The encoded pulse signal is preferably transmitted by means of amplitude modulation, e.g. on/off keying, of a carrier signal with a frequency in the low MHz range, e.g. about 1-10 MHz or about 2-5 MHz. Accordingly, the post-processor 7 preferably comprises a receiver 12 and the pulse generator 24. The receiver 12 receives the encoded pulse signal through the reception coil 6, decodes the encoded pulse signal into the pulse signal and provides the decoded pulse signal to the pulse generator 24. The pulse generator 24 generates the electric charge pulses in accordance with the emission times and target charge amounts E indicated in the decoded pulse signal as described further above.

The hearing-device configuration described above allows for performing a minimum of power-consuming computations and/or signal processing within the post-processor 7 and thus allows for supplying power to the post-processor 7 using the NFMI signals transmitted by the transmitter 11, e.g. by using these signals to charge a capacitor (not shown) comprised by the implantable stimulator 3. The transmission is performed using a transmission protocol that preferably allows for transmitting dummy signals in order to provide further power to the post-processor 7 in cases and/or during time periods wherein the power transmitted in the encoded pulse signal does not suffice. Other hearing-device configurations may be readily contemplated. However, the benefits of such other hearing-device configurations should be balanced against the possibly increased complexity of the circuits to be implanted, which may make the implantable stimulator 3 less robust and further increase its power consumption. Also, the amount of data to be transmitted to the implantable stimulator 3 may increase, which may require an increase in transmission bandwidth and further increase the complexity of the implanted receiver 12. In such other configurations, the transmitter 11 and the receiver 12 should obviously appear in the appropriate other functional blocks of the functional diagram.

Figure 3:
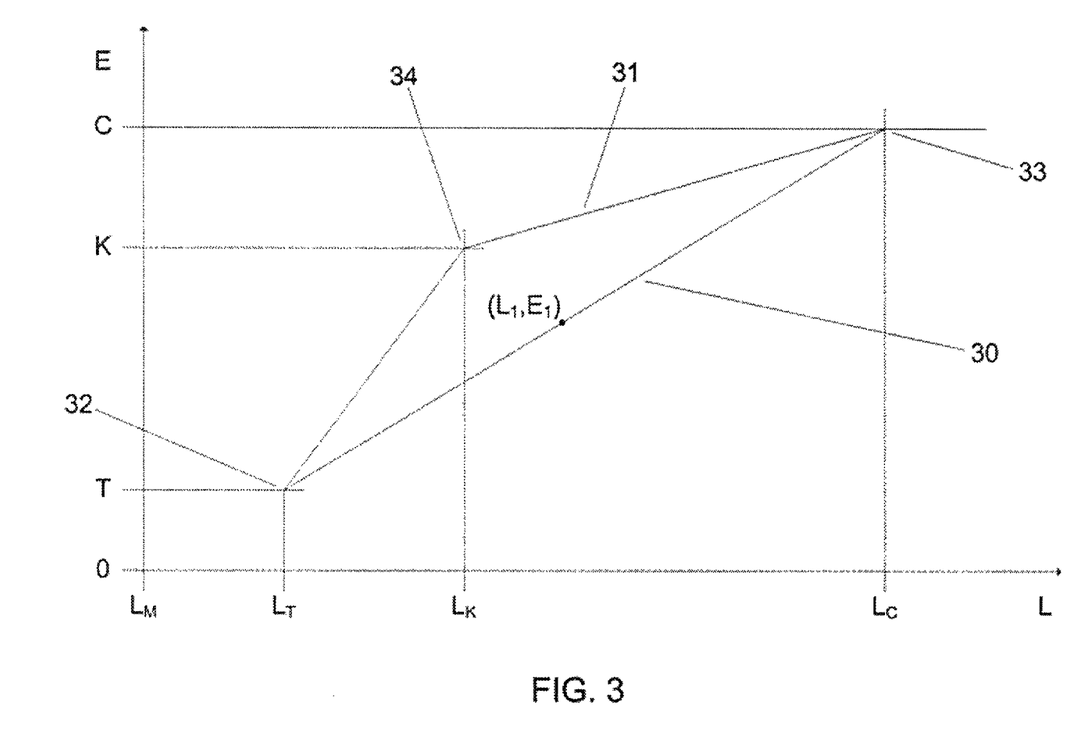
FIG. 3 shows a diagram illustrating the function of the hearing device shown in FIG. 1 according to an embodiment of the invention.

The diagram shown in FIG. 3 illustrates how target charge amounts E for the individual electric charge pulses in each pulse stream or auditory channel may be computed from the levels L of the respective noise-filtered signal using a piecewise linear mapping function, e.g. a simple mapping function 30 or an enhanced mapping function 31. The L axis and the E axis are both linear, and each mapping function 30, 31 maps the logarithm L of the sound pressure or the energy in the respective noise-filtered signal into a target charge amount E for the respective pulse stream or auditory channel. The mapping functions 30, 31 may differ between the auditory channels due to different coupling between the electrodes 10 and the neural fibres and/or different sensitivity in the different neural fibres.

A normal-hearing person has a frequency-dependent hearing threshold that defines the weakest sounds the person can hear and a frequency-dependent uncomfortable level (UCL) that defines the weakest sounds that cause discomfort in the person. In the following text, the term "comfortable acoustic range" refers to the frequency-dependent level range between the typical hearing threshold and the typical UCL for normal-hearing persons. Statistically obtained values for these levels are well known in the art. It is also well known that normal-hearing persons typically perceive loudness approximately logarithmic within the comfortable acoustic range. A specific relative increase, such as e.g. a doubling, of the sound pressure or the energy in an acoustic signal thus typically creates a perception of a specific absolute increase of loudness. This is reflected in the common use of the logarithmic dB scale for sound levels.

In contrast hereto, the perception of loudness when the auditory neural fibres are directly electrically stimulated is approximately linear within the dynamic range perceivable by the user. A specific absolute increase in the emitted electric charge thus typically creates a perception of a specific absolute increase of loudness, regardless of the starting loudness. The perception is, however, quite varying from person to person, and the hearing device 1 therefore needs to be calibrated to the individual user. After the implantation of the implantable stimulator 3, an audiologist thus normally performs one or more tests in order to determine which electrodes 10 are functional, which auditory channels may be stimulated and which stimulation levels may be perceived by the user in the individual auditory channels. For each auditory channel, the audiologist preferably determines a threshold charge T equal to the smallest charge that the user can perceive in charge pulses and a maximum comfortable charge C equal to the largest charge that the user can perceive in charge pulses emitted repeatedly for a longer time without feeling discomfort. In the following text, the term "comfortable stimulation range" refers to the level range between the threshold charge T and the maximum comfortable charge C for a particular auditory channel.

The input circuit 20, the filter bank 21 and the noise filter 22 together constitute a signal path taking the acoustic signal as input and providing the noise-filtered signal(s) as output. The portion of the signal path 20, 21, 22 preceding the noise filter 22 preferably applies a linear gain, i.e. a gain that is not level-dependent, to any acoustic signal within the comfortable acoustic range. Thus, the signal path 20, 21, 22 preceding the noise filter 22 neither causes an effective level compression nor an effective level expansion of noise-filtered signals derived from an acoustic signal having a level within the comfortable acoustic range. This preferably also applies to the noise filter 22. Electronic components used for implementing the signal path 20, 21, 22 are thus preferably dimensioned such that their inherent nonlinearities neither affect the band-limited audio signal nor the band-limited audio signal noise-filtered signals when these signals are derived from an acoustic signal having a level within the comfortable acoustic range. Alternatively, or additionally, the signal path 20, 21, 22 may comprise means for compensating for such nonlinearities in order to avoid both effective level compression and effective level expansion.

Also, the input gain, i.e. the total gain in the signal path 20, 21, 22, is preferably fixed or calibrated at known values. This allows the hearing device 1 to let the user perceive the loudness of an acoustic signal similarly strong as a normal-hearing person by mapping the comfortable acoustic range into the comfortable stimulation range such that an acoustic signal at the hearing threshold causes stimulation at the threshold charge T and an acoustic signal at the UCL causes stimulation at the maximum comfortable charge C in the respective auditory channel with a linear dependency between these end points. When the input gain is known, the noise signal level L may be computed as the sum of the level of the acoustic signal and the input gain, at least for a tonal acoustic signal that is not attenuated by the noise-filter 22, and thus, the linear mapping from the comfortable acoustic range into the comfortable stimulation range may be achieved by mapping a corresponding level range of the noise signals into target charge amount E, e.g. using the simple mapping function 30.

In each point (L, E), the mapping functions 30, 31 have a slope dE/dL, which for instance in the example point ($L_1$, $E_1$) determines how much the target charge amount E shall increase from $E_1$ when the noise-filtered signal level L increases from $L_1$. In the following, the slope dE/dL is referred to as the incremental gain $G_i$. The sound levels L provided to the mapping functions 30, 31 may attain negative, zero and/or positive values depending on the reference value for the signal levels L. On the other hand, the electric charge amounts E provided by the mapping functions 30, 31 are inherently non-negative. Note therefore, that an absolute gain is not well defined and that the unit of the incremental gain $G_i$ obviously depends on the respective units of the sound levels L and of the target charge amounts E.

The simple mapping function 30 preferably extends linearly between a lower knee point 32 and an upper knee point 33. In the lower knee point 32, the simple mapping function 30 maps a threshold level $L_T$ corresponding to the user's hearing threshold into the threshold charge T. In the upper knee point 33, the simple mapping function 30 maps a maximum comfortable level $L_C$ corresponding to the user's UCL into the maximum comfortable charge C. Between the lower and upper knee points 32, 33, the simple mapping function 30 has a constant and positive incremental gain $G_i$ of $(C-T)/(L_C-L_T)$.

Between the knee points 32, 33, the electric charge amounts emitted by the electrodes 10 thus increase with increasing noise-filtered signal levels L and thus with increasing levels of the acoustic signal. Signal levels L above the maximum comfortable level $L_c$ are preferably mapped into the maximum comfortable charge C and thus with zero incremental gain $G_i$ in order to avoid creating uncomfortable sensations in the user. Signal levels L below the threshold level $L_T$ are preferably mapped into zero charge C and thus with infinite incremental gain $G_i$ in order to save energy in the implantable stimulator 3. The noise-floor threshold of the noise filter 22 is preferably above and not below the threshold level $L_T$. The noise-floor threshold of the noise filter 22 may be set equal to the threshold level $L_T$ in order to allow the user to perceive acoustic signal levels within the entire comfortable acoustic range.

The computation of target charge amounts E using a piecewise linear mapping function, such as the simple mapping function 30, effectively amounts to applying a level-dependent gain in the hearing device 1. Such level compression and/or level expansion are commonly applied and thus well known in the art of hearing devices. However, by applying level compression and/or level expansion only after deriving the band-limited audio signals in the filter bank 21 and after attenuating undesired signal components in the noise filter 22, thus allowing the filter bank 21 and the noise filter 22 to operate on signals that have neither been subjected to effective level compression nor to effective level expansion, the amount of artefacts produced by the filter bank 21 and the noise filter 22 is substantially reduced. Furthermore, by applying level compression and/or level expansion only after deriving the band-limited audio signals in the filter bank 21 and after attenuating undesired signal components in the noise filter 22, parameters for level compression and/or level expansion may be set in a more deterministic way than in the prior art, i.e. in dependence on predefined levels of the received acoustic signal. Thus, predefined acoustic levels may be mapped to predefined stimulus levels, i.e. pulse charge amounts, which allows an audiologist to perform fitting of the hearing device 1 in a much more intuitive way than possible for prior art hearing devices.

The enhanced mapping function 31 deviates from the simple mapping function 30 only in that it extends from the lower knee point 32 to the upper knee point 33 via an intermediate knee point 34, such that the incremental gain $G_i$ is larger between the lower knee point 32 and the intermediate knee point 34 than between the intermediate knee point 34 and the upper knee point 33. In the intermediate knee point 34, the enhanced mapping function 31 maps an intermediate threshold level $L_K$ to an intermediate charge K. Compared to the simple mapping function 30, the enhanced mapping function 31 thus applies a level expansion to audible signal levels L below the intermediate threshold level $L_K$ and a level compression to comfortable signal levels L above the intermediate threshold level $L_K$.

The purpose of the intermediate knee point 34 is primarily to enhance information conveyed in speech and thus improve the user's ability to decode and understand speech. During typical conversations with moderate voice levels in quiet surroundings, the level of the speech signals received by the hearing device 1 normally concentrate within the lower portion of the comfortable acoustic range. The intermediate threshold level $L_K$ is therefore preferably determined in dependence on a statistic evaluation of typical speech situations such that the majority of the levels typically appearing in such speech situations is below the intermediate threshold level $L_K$. The influence of the input gain on the noise-filtered signal levels L should be appropriately considered in this determination. The intermediate charge K is preferably closer to the maximum comfortable charge C than to the threshold charge T. These two conditions on the intermediate knee point 34 are normally sufficient to place it above the curve of the simple mapping function 30. However, for some auditory channels and/or for some speech languages, they may not suffice. In this case, the simple mapping function 30 should be used instead of the enhanced mapping function 31 for the particular auditory channel(s). The intermediate knee point 34 ensures that the levels typically appearing in speech situations are mapped to a relatively larger range of target charge amounts E, which typically will improve the user's ability to understand the speech.

The enhanced mapping function 31 may be used also in such hearing devices 1 and/or signal processors 25 wherein the absence of effective level compression and effective level expansion applies only to a smaller portion than stated further above of the level range of the acoustic signal—or does not apply at all, even when this may increase the amount of artefacts. In such hearing devices 1 and/or signal processors 25, the location of the knee points 32, 33, 34 in the diagram of FIG. 3 may have to be adjusted to best fit the thus possibly level-dependent gain in the signal path 20, 21, 22.

In other embodiments, the intermediate threshold level $L_K$ may be determined such that about 60%, about 70%, about 80% or about 90% of the levels typically appearing in the speech situations are below the intermediate threshold level $L_K$. The determination of the intermediate threshold level $L_K$ may further be made based on preferences of the user or on knowledge about the user's hearing ability in general. Similarly, the intermediate charge K may be determined such that it is located at a distance from the threshold charge T equalling about 60%, about 70%, about 80% or about 90% of the distance between the threshold charge T and the maximum comfortable charge C. Also the determination of the intermediate charge K may further be based on preferences of the user and/or on knowledge about the user's hearing ability in general. For speech at a medium level in the French language, and for the average user, the intermediate knee point 34 may preferably be determined according to Table 1 below. The frequency ranges and the intermediate knee points 34 may vary, e.g. for other languages and for different users.

TABLE 1

| Frequency range | $L_K$ − (input gain) | (K − T)/(C − T) |
|---|---|---|
| 200 Hz-850 Hz | 61 $dB_{SPL}$ | 90% |
| 850 Hz-1500 Hz | 61 $dB_{SPL}$ | 90% |
| 1500 Hz-3450 Hz | 57 $dB_{SPL}$ | 90% |
| 3450 Hz-8000 Hz | 50 $dB_{SPL}$ | 90% |

Table 1 should be interpreted such that for noise-filtered signals mainly comprising frequencies within the frequency range 200 Hz-850 Hz, the intermediate threshold level $L_K$ should thus be set to 61 $dB_{SPL}$ plus the input gain for the respective frequency range, and the intermediate charge K should be set at 90% of the distance from the threshold charge T to the maximum comfortable charge C, etc. The knee points 34 defined by Table 1 are set such that about 90% of the information comprised in the listed speech frequency bands are below the respective intermediate threshold levels $L_K$.

Figure 4:
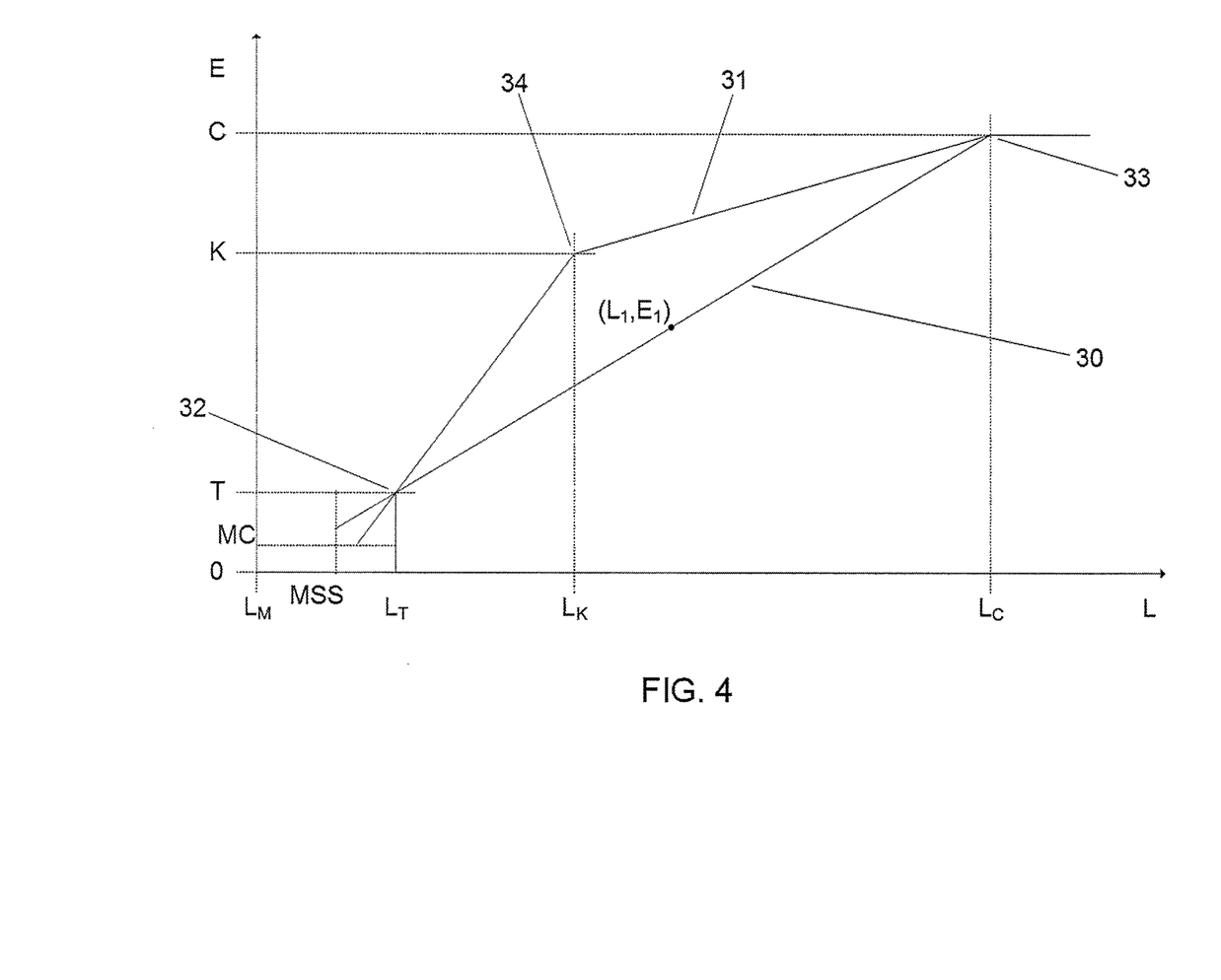
FIG. 4 shows a diagram illustrating the function of the hearing device shown in FIG. 1 according to another embodiment of the invention.

As described earlier; for each auditory channel, the threshold charge T equal to the smallest charge that the user can perceive in charge pulses is determined. The target charge amounts E for individual electric charge pulses in each pulse stream or auditory channel is mapped to the levels L of respective noise-filtered signal. For example, the threshold charge T is mapped to the threshold level $L_T$ of the comfortable acoustic range. Conventionally, signals lower than this minimum level do not stimulate the patient while the signal above stimulate the patient. In an embodiment (as represented in FIG. 4), for overcoming non-linearity on the behavior of the simulation that may be considerable for signals that are in average around the threshold level $L_T$, simulation below the threshold level is provided. This would be beneficial to the patient to the patient as the nerves would be on near simulation threshold when a signal level L is close to the threshold level $L_T$. As illustrated, the mapping functions 30, 31 is extended in a region where the noise-filtered signal level L is below the threshold level $L_T$. For the enhanced mapping function 31, such extension is made utilizing the slope dE/dL obtained between the lower knee point 32 and the intermediate knee point 34. Although, the extended simple mapping function 30 may be utilized for determining the stimulation but the extended enhanced mapping function is preferred. In such a scenario, the stimulation may be limited by either the minimum system sensitivity (MSS) or the absolute minimum capability (MC) of the implant such as 5 µs.

The hearing device 1 may preferably comprise a user-operable control (not shown), such as a control element on the wearable device 2 and/or on a wired or wireless remote control, that allows the user to adjust the intermediate threshold level $L_K$. The user-operable control preferably allows the user to adjust the intermediate threshold level $L_K$ in predefined level steps, such as e.g. 10 dB steps or 6 dB steps. This allows the user to adapt the signal processing in the signal processor 25 to weaker and/or louder speech. The signal processor 25 may preferably comprise an environment analyser (not shown) that analyses the acoustic signal and adjusts the intermediate threshold level $L_K$ in dependence on the analysis, such that the intermediate threshold level $L_K$ decreases when the signal processor 25 receives weaker speech signals and increases when the signal processor 25 receives louder speech signals. The signal processor 25 may thus automatically perform adjustments otherwise made by the user.

The hearing device 1 may preferably comprise a user-operable control (not shown) that allows the user to switch the hearing device between using the simple mapping function 30 and the enhanced mapping function 31 for relevant auditory channels, i.e. those auditory channels having an intermediate knee point 34 above the simple mapping function 30. This allows the user to adapt the signal processing in the hearing device 1 to situations with and without speech. Thus, when speech is present, the user may choose signal processing than enhances speech, and when speech is absent, the user may choose signal processing that provides a more natural loudness curve, e.g. for environmental sounds. The signal processor 25 may preferably comprise a speech detector that detects speech in the acoustic signal and switches the signal processor 25 to using the enhanced mapping function 31 for the relevant auditory channels when detecting speech and switches the signal processor 25 to using the simple mapping function 30 when speech is absent, thus automatically performing switching otherwise made by the user.

In some embodiments, the used mapping functions 30, 31 may have further knee points. In some embodiments, the mapping functions 30, 31 may above the upper knee point 33 have a positive incremental gain $G_i$ that is smaller than the incremental gain $G_i$ between the lower and the upper knee points 32, 33. In some embodiments, the mapping functions 30, 31 may have an incremental gain $G_i$ that is zero or positive and finite below the lower knee point 32. The knee points 32, 33, 34 are preferably implemented as soft knee points, i.e. such that the incremental gain $G_i$ transitions smoothly in the immediate vicinity of the knee points 32, 33, 34, in order to avoid abrupt changes of the incremental gain $G_i$ in the knee points 32, 33, 34. In some embodiments, the incremental gain $G_i$ may be only approximately constant, and the mapping functions 30, 31 may be only approximately piecewise linear.

The signal processor 25 is preferably implemented mainly as digital circuits operating in the discrete time domain, but any or all parts hereof may alternatively be implemented as analog circuits operating in the continuous time domain. Digital functional blocks of the hearing device 1, such as e.g. the pre-emphasis filter 204, the filter bank 21, the noise filter 22, the pulse controller 23, the transmitter 11, the receiver 12 and the pulse generator 24 may be implemented in any suitable combination of hardware, firmware and software and/or in any suitable combination of hardware units. Furthermore, any single hardware unit may execute the operations of several functional blocks in parallel or in interleaved sequence and/or in any suitable combination thereof.

The hearing device 1 may be part of a binaural hearing system.

Further modifications obvious to the skilled person may be made to the disclosed apparatus and/or method without deviating from the scope of the invention. Within this description, any such modifications are mentioned in a non-limiting way.

Some preferred embodiments have been described in the foregoing, but it should be stressed that the invention is not limited to these, but may be embodied in other ways within the subject-matter defined in the following claims. For example, the features of the described embodiments may be combined arbitrarily, e.g. in order to adapt the system, the apparatus and/or the method according to the invention to specific requirements.

It is further intended that the structural features of the apparatus described above, in the detailed description of 'mode(s) for carrying out the invention' and in the claims can be combined with the methods, when appropriately substituted by a corresponding process. Embodiments of the methods have the same advantages as the corresponding apparatus.

Any reference numerals and names in the claims are intended to be non-limiting for their scope.

The invention claimed is:

1. A hearing aid system, comprising:
    an implantable stimulator including two or more electrodes for emitting electric charge pulses to neural fibres of an individual; and
    a signal processor circuit including
        an input circuit configured to receive an acoustic signal from the individual's surroundings and provide at least one corresponding input audio signal,
        a filter bank configured to receive the at least one input audio signal and to output at least one band-limited audio signal in dependence on the at least one input audio signal, and
        a noise filter configured to attenuate undesired signal components in the at least one band-limited audio signal and to provide at least one corresponding noise-filtered signal, wherein
    the input circuit and the filter bank are configured to prevent an effective level compression and an effective level expansion of the at least one noise-filtered signal when the input circuit and the filter bank process the acoustic signal having a level within the individual's predefined comfortable acoustic range.

2. The hearing aid system according to claim 1, wherein the signal processor further includes
    a pulse controller configured to control the emission of the electric charge pulses for at least one auditory channel in dependence on the at least one noise-filtered signal, such that the amount of electric charge provided in the electric charge pulses increases with increasing level of the at least one noise-filtered signal, thereby defining at least one level-dependent incremental gain.

3. The hearing aid system according to claim 2, wherein the pulse controller is further configured to control the incremental gain such that it is larger for any level of the at least one noise-filtered signal between a lower threshold level and an upper threshold level than for any level above the upper threshold level.

4. The hearing aid system according to claim 3, wherein the pulse controller is further configured to control the incremental gain such that it is larger for any level of the at least one noise-filtered signal between the lower threshold level and an intermediate threshold level than for any level between the intermediate threshold level and the upper threshold level.

5. The hearing aid system according to claim 4, wherein the signal processor further includes
    an environment analyser configured to analyse the acoustic signal in the individual's environment and adjust the intermediate threshold level in dependence on the analysis, such that the intermediate threshold level decreases when the signal processor receives weaker speech signals and increases when the signal processor receives louder speech signals.

6. The hearing aid system according to claim 4, further the signal processor is configured to
    control the intermediate threshold level in dependence on input provided by the individual.

7. The hearing aid system according to claim 3, wherein the level thresholds are determined to correspond with respective predetermined threshold levels of the acoustic signal.

8. The hearing aid system according to claim 3, wherein the pulse controller is further configured to control the incremental gain such that it filtered signal between the lower level threshold and the upper level threshold, except for smooth transitions in the immediate vicinity of the level thresholds.

9. The hearing aid system according to claim 1, wherein the input circuit comprises:
    an input transducer configured to receive the acoustic signal and provide a corresponding electric input signal;
    a pre-amplifier configured to apply a linear gain to the electric input signal, the gain being independent of the level of the electric input signal;
    a digitiser configured to digitise the electric input signal after pre-amplification and to provide the digitised signal as the input audio signal; and
    a pre-emphasis filter that is configured based on a hearing capability of the individual to achieve a human-ear's natural frequency characteristic.

10. The hearing aid system according to claim 1, wherein the filter bank comprises:
    a time-to-frequency domain converter configured to provide a set of narrow-band frequency signals in dependence on the input audio signal; and
    a channel combiner configured to provide the at least one band-limited audio signal as a sum or an energy sum of a subset of the set of narrow-band frequency signals.

11. A wearable device comprising a hearing aid system according to claim 1.

12. A method for operating a hearing device with an implantable stimulator having two or more electrodes for emitting electric charge pulses to neural fibres of an individual, the method comprising:
  receiving an acoustic signal from the individual's surroundings and providing a corresponding input audio signal;
  inputting the input audio signal to a filter bank and outputting at least one band-limited audio signal in dependence on the input audio signal;
  inputting the at least one band-limited audio signal to a noise filter and attenuating undesired signal components in the at least one band-limited audio signal and providing at least one corresponding noise-filtered signal;
  preventing an effective level compression and an effective level expansion of at least one band-limited audio signal prior to the attenuating of the undesired signal components by the noise filter; and
  controlling emission of the electric charge pulses for at least one auditory channel in dependence on the at least one noise-filtered signal, such that the amount of electric charge provided in the electric charge pulses increases with increasing level of the at least one noise-filtered signal, thereby defining at least one level-dependent incremental gain.

13. A method according to claim 12, and further comprising controlling the incremental gain such that it is larger for any level of the at least one noise-filtered signal between a lower threshold level and an upper threshold level than for any level above the upper threshold level.

14. A method according to claim 13, and further comprising
  controlling the incremental gain such that it is larger for any level of the at least one noise-filtered signal between the lower threshold level and an intermediate threshold level than for any level between the intermediate threshold level and the upper threshold level.

15. A wearable device comprising the hearing aid system according to claim 2.

16. A wearable device comprising the hearing aid system according to claim 3.

17. A wearable device comprising the hearing aid system according to claim 4.

18. A wearable device comprising the hearing aid system according to claim 5.

19. A wearable device comprising the hearing aid system according to claim 6.

* * * * *